US006962986B2

(12) United States Patent
Viviani et al.

(10) Patent No.: US 6,962,986 B2
(45) Date of Patent: Nov. 8, 2005

(54) NUCLEIC ACID MOLECULES ENCODING RED AND GREEN EMITTING LUCIFERASES

(75) Inventors: Vadim R. Viviani, Somerville, MA (US); Yoshihiro Ohmiya, Shizuoka (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/993,874

(22) Filed: Nov. 14, 2001

(65) Prior Publication Data

US 2002/0119542 A1 Aug. 29, 2002

Related U.S. Application Data

(63) Continuation of application No. 09/516,958, filed on Mar. 1, 2000, now abandoned, which is a continuation-in-part of application No. 09/388,290, filed on Sep. 1, 1999, now abandoned.

(51) Int. Cl.[7] .......................... C07H 21/04; C12N 9/02; C12N 1/21; C12N 15/52
(52) U.S. Cl. ................... 536/23.2; 435/189; 435/252.3; 435/252.33; 435/320.1; 435/325; 435/410
(58) Field of Search .............................. 536/23.2, 23.5; 435/189, 252.3, 252.33, 320.1, 325, 410, 69.1

(56) References Cited

U.S. PATENT DOCUMENTS 5,700,673 A 12/1997 McElroy et al. ............ 435/189

OTHER PUBLICATIONS

Viviani et al. (Jun. 29, 1999) Biochemistry, vol. 38 (26), pp. 8271–8279.
Viviani, V.R., et al., "Bioluminescence Color Determinants of *Phrixothrix* Railroad-worm Luciferases: Chimeric Luciferases, Site-directed Mutagenesis of Arg 215 and Guanidine effect", *Photochemistry and Photobiology*, 72(2):267–271 (2000).
GeneBank database (Jun. 2, 1999) Accession.
GeneBank database (Jun. 2, 1999) Accession.
Viviani et al., "Cloning and Characterization of cDNAs for *Phrixothrix* app (Coleoptera:Phenogodidae) Railroad–Worms Luciferases", *J. Biolumin Chemilumin.*, 13:239 (1998) Abstract from the 10th International Symposium on Bioluminescence & Clemiluminescence, Bologna, Italy Sep. 4–8, 1998.
Viviani, et al., "Thr226 is a Key Residue for Biolumines-cence Spectra Determination in Beetle Luciferases", *Biochem. and Biophys. Research Commun.*, 280:1286–1291 (2001).
Vadim R. Viviani, et al., "Biophysical and Biochemical Aspects of Phengodid (Railroad–Worm) Bioluminescence," *Photochemistry and Photobiology*, vol. 58, No. 4, pp. 615–622 (1993).

(Continued)

*Primary Examiner*—Elizabeth Slobodyansky
(74) *Attorney, Agent, or Firm*—Knobbe, Martens, Olson & Bear LLP

(57) ABSTRACT

Isolated nucleic acid molecules which code for luciferases able to produce the green bioluminescence of *Phrixotrhix vivianii* and red bioluminescence of *Phrixothrix hirtus* are described. The nucleic acid molecules and the luciferases encoded thereby can be used in applications such as diagnostic methods and molecular biology tools.

3 Claims, 1 Drawing Sheet

OTHER PUBLICATIONS

Vadim R. Viviani, et al., "Bioluminescence of Brazilian Fireflies (Coleoptera: Lampyridae): Spectral Distribution and pH Effects on Luciferase–Elicited Colors. Comparison with Elaterid and Phengodid Luciferases," Photochemistry and Photobiology, vol. 62, No. 3, pp. 490–495 (1995).

Vadim R. Viviani, et al., "Bioluminescence and Biological Aspects of Brazilian Railroad–Worms (Coleoptera: Phengodidae)," Annals of the Entomological Society of America, vol. 90 No. 3, pp. 389–398 (1997).

VR Viviani et al., "Cloning and Characterization of cDNA for the Larval Click–Beetle *Pyrearinus termitilluminans* (Coleoptera:Elateridae) Luciferase," Proceedings of the $10^{th}$ International Symposium on Bioluminescence and Chemiluminescence, Bologna, Italy, John Wiley & Sons, New York, pp. 384–387 (1999).

SEQUENCE LISTING

<160> NUMBER OF SEQ ID NOS: 4

<210> SEQ ID NO 1
<211> LENGTH: 1765
<212> TYPE: DNA
<213> ORGANISM: Phrixothrix vivianii
<220> FEATURE:
<221> NAME/KEY: CDS
<222> LOCATION: (26)...(1660)

<400> SEQUENCE: 1

```
tcagtgcaag actttaggga tcaaa atg gaa gaa gaa aac att agg cat gga         52
                              Met Glu Glu Glu Asn Ile Arg His Gly
                                1               5 gag cgt cct cgt gat ata gtc cat cct ggc tcg gca gga caa caa tta        100
Glu Arg Pro Arg Asp Ile Val His Pro Gly Ser Ala Gly Gln Gln Leu
 10              15                  20                  25 tac caa tca ttg tat aaa ttt gca tct ttt cct gaa gca ata atc gat        148
Tyr Gln Ser Leu Tyr Lys Phe Ala Ser Phe Pro Glu Ala Ile Ile Asp
                 30                  35                  40 gct cat aca aat gaa gta ata tca tat gct caa ata ttt gaa acc agc        196
Ala His Thr Asn Glu Val Ile Ser Tyr Ala Gln Ile Phe Glu Thr Ser
             45                  50                  55 tgc cgc tta gct gtt agt ata gaa caa tat ggc ttg aat gaa aac aat        244
Cys Arg Leu Ala Val Ser Ile Glu Gln Tyr Gly Leu Asn Glu Asn Asn
         60                  65                  70 gtt gtt ggt gta tgc agt gaa aac aat ata aac ttt ttt aat cct gtc        292
Val Val Gly Val Cys Ser Glu Asn Asn Ile Asn Phe Phe Asn Pro Val
     75                  80                  85 ctt gct gct tta tac tta gga ata cca gta gca aca tca aat gat atg        340
Leu Ala Ala Leu Tyr Leu Gly Ile Pro Val Ala Thr Ser Asn Asp Met
 90                  95                 100                 105 tac aca gat gga gag tta act ggt cat ttg aat ata tca aaa cca act        388
Tyr Thr Asp Gly Glu Leu Thr Gly His Leu Asn Ile Ser Lys Pro Thr
                110                 115                 120 atc atg ttt agt tca aag aaa gca ctc ccg ctt att ctg aga gta cag        436
Ile Met Phe Ser Ser Lys Lys Ala Leu Pro Leu Ile Leu Arg Val Gln
            125                 130                 135 caa aat cta agt ttc att aaa aaa gtc gta gtt atc gat agc atg tac        484
Gln Asn Leu Ser Phe Ile Lys Lys Val Val Val Ile Asp Ser Met Tyr
        140                 145                 150 gac att aat ggc gtt gaa tgc gta tct acc ttt gtt gca cgt tat act        532
Asp Ile Asn Gly Val Glu Cys Val Ser Thr Phe Val Ala Arg Tyr Thr
    155                 160                 165 gac cac acc ttt gat cca ttg tca ttt aca cca aaa gat ttt gat ccc        580
Asp His Thr Phe Asp Pro Leu Ser Phe Thr Pro Lys Asp Phe Asp Pro
170                 175                 180                 185 ctt gaa aaa atc gca tta att atg tca tca tct gga aca act gga ttg        628
Leu Glu Lys Ile Ala Leu Ile Met Ser Ser Ser Gly Thr Thr Gly Leu
                190                 195                 200 cct aag ggt gta gta ctg agc cat aga agt cta act ata aga ttc gtt        676
Pro Lys Gly Val Val Leu Ser His Arg Ser Leu Thr Ile Arg Phe Val
            205                 210                 215 cat agc agg gat ccc att tat ggc act cgt acg gtt cca caa aca tca        724
His Ser Arg Asp Pro Ile Tyr Gly Thr Arg Thr Val Pro Gln Thr Ser
        220                 225                 230 att ctt tcc tta gta ccg ttc cat cat gcc ttt gga atg ttt act aca        772
Ile Leu Ser Leu Val Pro Phe His His Ala Phe Gly Met Phe Thr Thr
    235                 240                 245 tta tct tac ttt gta gta gga ctt aag gtt gta atg ttg aag aaa ttt        820
Leu Ser Tyr Phe Val Val Gly Leu Lys Val Val Met Leu Lys Lys Phe
250                 255                 260                 265 gag ggc gca ctt ttc tta aaa acc ata cag aat tac aaa atc ccc act        868
Glu Gly Ala Leu Phe Leu Lys Thr Ile Gln Asn Tyr Lys Ile Pro Thr
                270                 275                 280 att gta gtg gcc cct cca gtt atg gtg ttt ttg gct aaa agc cca tta        916
Ile Val Val Ala Pro Pro Val Met Val Phe Leu Ala Lys Ser Pro Leu
            285                 290                 295
```

```
gtc gat caa tac gat tta tcg agc tta acg gaa gtt gct act gga gga       964
Val Asp Gln Tyr Asp Leu Ser Ser Leu Thr Glu Val Ala Thr Gly Gly
            300                 305                 310 gct cct tta gga aaa gat gtc gca gaa gca gta gca aag agg ttg aaa      1012
Ala Pro Leu Gly Lys Asp Val Ala Glu Ala Val Ala Lys Arg Leu Lys
        315                 320                 325 tta cct gga atc ata caa gga tat gga tta act gaa act tgc tgc gct      1060
Leu Pro Gly Ile Ile Gln Gly Tyr Gly Leu Thr Glu Thr Cys Cys Ala
330                 335                 340                 345 gta atg att acc cct cat aat gct gtg aaa aca ggt tca act gga aga      1108
Val Met Ile Thr Pro His Asn Ala Val Lys Thr Gly Ser Thr Gly Arg
                350                 355                 360 ccc ttg cca tac att aaa gct aaa gtt tta gat aac gct act ggg aag      1156
Pro Leu Pro Tyr Ile Lys Ala Lys Val Leu Asp Asn Ala Thr Gly Lys
            365                 370                 375 gcg cta gga cca gga gaa aga ggc gaa ata tgc ttt caa agt gaa atg      1204
Ala Leu Gly Pro Gly Glu Arg Gly Glu Ile Cys Phe Gln Ser Glu Met
        380                 385                 390 att atg aaa gga tat tac aac aat ccg gaa gca act att gat act att      1252
Ile Met Lys Gly Tyr Tyr Asn Asn Pro Glu Ala Thr Ile Asp Thr Ile
395                 400                 405 gac aaa gat ggt tgg ctt cat tct gga gat att gga tat tac gac gaa      1300
Asp Lys Asp Gly Trp Leu His Ser Gly Asp Ile Gly Tyr Tyr Asp Glu
410                 415                 420                 425 gat gga aat ttc ttt ata gtt gat cga ttg aaa gaa ctt att aaa tac      1348
Asp Gly Asn Phe Phe Ile Val Asp Arg Leu Lys Glu Leu Ile Lys Tyr
                430                 435                 440 aag gga tat cag gtt gcg cct gct gaa ctg gaa aat ctg ctt tta caa      1396
Lys Gly Tyr Gln Val Ala Pro Ala Glu Leu Glu Asn Leu Leu Leu Gln
            445                 450                 455 cat cca agt att gct gat gcg ggt gtt act gga gtt ccg gac gaa ttt      1444
His Pro Ser Ile Ala Asp Ala Gly Val Thr Gly Val Pro Asp Glu Phe
        460                 465                 470 ggt gga caa tta cct gct gct tgt gtt gtg tta gaa tct ggc aag acg      1492
Gly Gly Gln Leu Pro Ala Ala Cys Val Val Leu Glu Ser Gly Lys Thr
475                 480                 485 ctg act gaa aag gaa gtt caa gat ttt att gca gca caa gtc act cca      1540
Leu Thr Glu Lys Glu Val Gln Asp Phe Ile Ala Ala Gln Val Thr Pro
490                 495                 500                 505 aca aag cat ctt cga ggc ggt gtc gta ttt gta gac agt att ccg aaa      1588
Thr Lys His Leu Arg Gly Gly Val Val Phe Val Asp Ser Ile Pro Lys
                510                 515                 520 ggc cct act gga aaa ctc atc aga aag gag ctc cga gaa ata ttt gcc      1636
Gly Pro Thr Gly Lys Leu Ile Arg Lys Glu Leu Arg Glu Ile Phe Ala
            525                 530                 535 cag cga gca cca aaa tca aaa tta taagttcaat gtattgcttt agttctaaaa    1690
Gln Arg Ala Pro Lys Ser Lys Leu
        540                 545 tgtatataaa caagttttag aacctaatac attcattcaa atactaaaca aaaaaaaaa    1750 aaaaaaaaaa aaaaa                                                     1765

<210> SEQ ID NO 2
<211> LENGTH: 545
<212> TYPE: PRT
<213> ORGANISM: Phrixothrix vivianii

<400> SEQUENCE: 2

Met Glu Glu Glu Asn Ile Arg His Gly Glu Arg Pro Arg Asp Ile Val
1               5                   10                  15
```

-continued

```
His Pro Gly Ser Ala Gly Gln Gln Leu Tyr Gln Ser Leu Tyr Lys Phe
             20                  25                  30

Ala Ser Phe Pro Glu Ala Ile Ile Asp Ala His Thr Asn Glu Val Ile
         35                  40                  45

Ser Tyr Ala Gln Ile Phe Glu Thr Ser Cys Arg Leu Ala Val Ser Ile
 50                  55                  60

Glu Gln Tyr Gly Leu Asn Glu Asn Val Val Gly Val Cys Ser Glu
 65                  70                  75                  80

Asn Asn Ile Asn Phe Phe Asn Pro Val Leu Ala Ala Leu Tyr Leu Gly
                 85                  90                  95

Ile Pro Val Ala Thr Ser Asn Asp Met Tyr Thr Asp Gly Glu Leu Thr
            100                 105                 110

Gly His Leu Asn Ile Ser Lys Pro Thr Ile Met Phe Ser Ser Lys Lys
            115                 120                 125

Ala Leu Pro Leu Ile Leu Arg Val Gln Gln Asn Leu Ser Phe Ile Lys
130                 135                 140

Lys Val Val Val Ile Asp Ser Met Tyr Asp Ile Asn Gly Val Glu Cys
145                 150                 155                 160

Val Ser Thr Phe Val Ala Arg Tyr Thr Asp His Thr Phe Asp Pro Leu
                165                 170                 175

Ser Phe Thr Pro Lys Asp Phe Asp Pro Leu Glu Lys Ile Ala Leu Ile
            180                 185                 190

Met Ser Ser Gly Thr Thr Gly Leu Pro Lys Gly Val Val Leu Ser
            195                 200                 205

His Arg Ser Leu Thr Ile Arg Phe Val His Ser Arg Asp Pro Ile Tyr
            210                 215                 220

Gly Thr Arg Thr Val Pro Gln Thr Ser Ile Leu Ser Leu Val Pro Phe
225                 230                 235                 240

His His Ala Phe Gly Met Phe Thr Thr Leu Ser Tyr Phe Val Val Gly
                245                 250                 255

Leu Lys Val Val Met Leu Lys Lys Phe Glu Gly Ala Leu Phe Leu Lys
            260                 265                 270

Thr Ile Gln Asn Tyr Lys Ile Pro Thr Ile Val Val Ala Pro Pro Val
            275                 280                 285

Met Val Phe Leu Ala Lys Ser Pro Leu Val Asp Gln Tyr Asp Leu Ser
            290                 295                 300

Ser Leu Thr Glu Val Ala Thr Gly Gly Ala Pro Leu Gly Lys Asp Val
305                 310                 315                 320

Ala Glu Ala Val Ala Lys Arg Leu Lys Leu Pro Gly Ile Ile Gln Gly
                325                 330                 335

Tyr Gly Leu Thr Glu Thr Cys Cys Ala Val Met Ile Thr Pro His Asn
            340                 345                 350

Ala Val Lys Thr Gly Ser Thr Gly Arg Pro Leu Pro Tyr Ile Lys Ala
            355                 360                 365

Lys Val Leu Asp Asn Ala Thr Gly Lys Ala Leu Gly Pro Gly Glu Arg
    370                 375                 380

Gly Glu Ile Cys Phe Gln Ser Glu Met Ile Met Lys Gly Tyr Tyr Asn
385                 390                 395                 400

Asn Pro Glu Ala Thr Ile Asp Thr Ile Asp Lys Asp Gly Trp Leu His
                405                 410                 415

Ser Gly Asp Ile Gly Tyr Tyr Asp Glu Asp Gly Asn Phe Phe Ile Val
            420                 425                 430
```

```
Asp Arg Leu Lys Glu Leu Ile Lys Tyr Lys Gly Tyr Gln Val Ala Pro
        435                 440                 445

Ala Glu Leu Glu Asn Leu Leu Gln His Pro Ser Ile Ala Asp Ala
    450                 455                 460

Gly Val Thr Gly Val Pro Asp Glu Phe Gly Gln Leu Pro Ala Ala
465                 470                 475                 480

Cys Val Val Leu Glu Ser Gly Lys Thr Leu Thr Glu Lys Val Gln
                485                 490                 495

Asp Phe Ile Ala Ala Gln Val Thr Pro Thr Lys His Leu Arg Gly Gly
            500                 505                 510

Val Val Phe Val Asp Ser Ile Pro Lys Gly Pro Thr Gly Lys Leu Ile
        515                 520                 525

Arg Lys Glu Leu Arg Glu Ile Phe Ala Gln Arg Ala Pro Lys Ser Lys
530                 535                 540

Leu
545

<210> SEQ ID NO 3
<211> LENGTH: 1760
<212> TYPE: DNA
<213> ORGANISM: Phrixothrix hirtus
<220> FEATURE:
<221> NAME/KEY: CDS
<222> LOCATION: (41)...(1678)

<400> SEQUENCE: 3
gtgacagttt agttcagtag aagatttttt tgagatcaaa atg gaa gaa gaa aac        55
                                             Met Glu Glu Glu Asn
                                               1               5 gtt gtg aat gga gat cgt cct cgt gat cta gtt ttt cct ggc aca gca       103
Val Val Asn Gly Asp Arg Pro Arg Asp Leu Val Phe Pro Gly Thr Ala
             10                  15                  20 gga cta caa tta tat caa tca tta tat aaa tat tca tat att act gac       151
Gly Leu Gln Leu Tyr Gln Ser Leu Tyr Lys Tyr Ser Tyr Ile Thr Asp
         25                  30                  35 gga ata atc gat gcc cat acc aat gaa gta ata tca tat gct caa ata       199
Gly Ile Ile Asp Ala His Thr Asn Glu Val Ile Ser Tyr Ala Gln Ile
     40                  45                  50 ttt gaa acc agc tgc cgc ttg gca gtt agt cta gaa aaa tat ggc ttg       247
Phe Glu Thr Ser Cys Arg Leu Ala Val Ser Leu Glu Lys Tyr Gly Leu
 55                  60                  65 gat cat aac aat gtt gtg gca ata tgc agt gaa aac aac ata cac ttt       295
Asp His Asn Asn Val Val Ala Ile Cys Ser Glu Asn Asn Ile His Phe
 70                  75                  80                  85 ttt ggc cct tta att gct gct tta tac caa gga ata cca atg gca aca       343
Phe Gly Pro Leu Ile Ala Ala Leu Tyr Gln Gly Ile Pro Met Ala Thr
                 90                  95                 100 tca aat gat atg tac aca gaa agg gag atg att ggc cat ttg aat ata       391
Ser Asn Asp Met Tyr Thr Glu Arg Glu Met Ile Gly His Leu Asn Ile
            105                 110                 115 tcg aaa cca tgc ctt atg ttt tgt tca aag aaa tca ctc cca ttt att       439
Ser Lys Pro Cys Leu Met Phe Cys Ser Lys Lys Ser Leu Pro Phe Ile
        120                 125                 130 ctg aaa gta caa aaa cat cta gat ttc ctt aaa aga gtc ata gtc att       487
Leu Lys Val Gln Lys His Leu Asp Phe Leu Lys Arg Val Ile Val Ile
    135                 140                 145 gat agt atg tac gat atc aat ggc gtt gaa tgc gta ttt agc ttt gat       535
Asp Ser Met Tyr Asp Ile Asn Gly Val Glu Cys Val Phe Ser Phe Asp
150                 155                 160                 165
```

-continued

| | |
|---|---|
| tca cgt aat act gat cac gcc ttt gat cca gtg aaa ttt aac cca aaa<br>Ser Arg Asn Thr Asp His Ala Phe Asp Pro Val Lys Phe Asn Pro Lys<br>170               175               180 | 583 |
| gag ttt gat ccc ttg gaa aga acc gca tta att atg aca tca tct gga<br>Glu Phe Asp Pro Leu Glu Arg Thr Ala Leu Ile Met Thr Ser Ser Gly<br>    185               190               195 | 631 |
| aca act gga ttg cct aaa ggg gta gta ata agc cat aga agt ata act<br>Thr Thr Gly Leu Pro Lys Gly Val Val Ile Ser His Arg Ser Ile Thr<br>200               205               210 | 679 |
| ata aga ttc gtc cat agc agt gat ccc atc tat ggt act cgt att gct<br>Ile Arg Phe Val His Ser Ser Asp Pro Ile Tyr Gly Thr Arg Ile Ala<br>    215               220               225 | 727 |
| cca gat aca tca att ctt gct ata gca ccg ttc cat cat gcc ttt gga<br>Pro Asp Thr Ser Ile Leu Ala Ile Ala Pro Phe His His Ala Phe Gly<br>230               235               240               245 | 775 |
| ctg ttt act gca cta gct tac ttt cca gta gga ctt aag att gta atg<br>Leu Phe Thr Ala Leu Ala Tyr Phe Pro Val Gly Leu Lys Ile Val Met<br>            250               255               260 | 823 |
| gtg aag aaa ttt gag ggc gaa ttc ttc tta aaa acc ata caa aat tac<br>Val Lys Lys Phe Glu Gly Glu Phe Phe Leu Lys Thr Ile Gln Asn Tyr<br>        265               270               275 | 871 |
| aaa atc gct tct att gta gtt cct cct cca att atg gta tat ttg gct<br>Lys Ile Ala Ser Ile Val Val Pro Pro Pro Ile Met Val Tyr Leu Ala<br>            280               285               290 | 919 |
| aaa agt cca tta gtc gat gaa tac aat tgc tcg agc tta acg gaa att<br>Lys Ser Pro Leu Val Asp Glu Tyr Asn Cys Ser Ser Leu Thr Glu Ile<br>295               300               305 | 967 |
| gct agt gga ggc tct cct tta gga aga gat atc gca gat aaa gta gca<br>Ala Ser Gly Gly Ser Pro Leu Gly Arg Asp Ile Ala Asp Lys Val Ala<br>310               315               320               325 | 1015 |
| aag aga ttg aaa gta cat gga atc cta caa gga tat gga tta acc gaa<br>Lys Arg Leu Lys Val His Gly Ile Leu Gln Gly Tyr Gly Leu Thr Glu<br>            330               335               340 | 1063 |
| acc tgc agc gct cta ata ctt agc ccc aat gat cga gaa ctt aaa aaa<br>Thr Cys Ser Ala Leu Ile Leu Ser Pro Asn Asp Arg Glu Leu Lys Lys<br>        345               350               355 | 1111 |
| ggt gca att gga acg cct atg cca tat gtt caa gtt aaa gtt ata gat<br>Gly Ala Ile Gly Thr Pro Met Pro Tyr Val Gln Val Lys Val Ile Asp<br>            360               365               370 | 1159 |
| atc aat act ggg aag gcg cta gga cca aga gaa aaa ggc gaa ata tgc<br>Ile Asn Thr Gly Lys Ala Leu Gly Pro Arg Glu Lys Gly Glu Ile Cys<br>375               380               385 | 1207 |
| ttc aaa agt caa atg ctt atg aaa gga tat cac aac aat ccg caa gca<br>Phe Lys Ser Gln Met Leu Met Lys Gly Tyr His Asn Asn Pro Gln Ala<br>390               395               400               405 | 1255 |
| act cgt gat gct ctt gac aaa gat ggt tgg ctt cat act ggg gat ctt<br>Thr Arg Asp Ala Leu Asp Lys Asp Gly Trp Leu His Thr Gly Asp Leu<br>            410               415               420 | 1303 |
| gga tat tac gac gaa gac aga ttt atc tat gta gtt gat cga ttg aaa<br>Gly Tyr Tyr Asp Glu Asp Arg Phe Ile Tyr Val Val Asp Arg Leu Lys<br>        425               430               435 | 1351 |
| gaa ctt att aaa tat aaa gga tat cag gtt gcg cct gct gaa ctg gaa<br>Glu Leu Ile Lys Tyr Lys Gly Tyr Gln Val Ala Pro Ala Glu Leu Glu<br>            440               445               450 | 1399 |
| aat ctg ctt tta caa cat cca aat att tct gat gcg ggt gtt att gaa<br>Asn Leu Leu Leu Gln His Pro Asn Ile Ser Asp Ala Gly Val Ile Glu<br>455               460               465 | 1447 |
| ttc cgg acg aat ttg ctg gtc aat tac ctt tcc gcg tgt gtt gtg tta<br>Phe Arg Thr Asn Leu Leu Val Asn Tyr Leu Ser Ala Cys Val Val Leu<br>470               475               480               485 | 1495 |

```
gag cct ggt aag aca atg acc gaa aag gaa gtt cag gat tat att gca    1543
Glu Pro Gly Lys Thr Met Thr Glu Lys Glu Val Gln Asp Tyr Ile Ala
            490                 495                 500 gag cta gtc act aca act aaa cat ctt cga ggc ggt gtc gta ttt ata    1591
Glu Leu Val Thr Thr Thr Lys His Leu Arg Gly Gly Val Val Phe Ile
        505                 510                 515 gat agt att cca aaa ggc cca aca gga aaa ctc atg aga aac gaa ctc    1639
Asp Ser Ile Pro Lys Gly Pro Thr Gly Lys Leu Met Arg Asn Glu Leu
        520                 525                 530 cga gca ata ttt gcc cgg gaa cag gca aaa tca aaa tta taagctcaat     1688
Arg Ala Ile Phe Ala Arg Glu Gln Ala Lys Ser Lys Leu
        535                 540                 545 atattgcttt agttataaaa tgtatgtaat caaattttag aacctaatac attcattgag  1748
agcctaaaaa aa                                                      1760

<210> SEQ ID NO 4
<211> LENGTH: 546
<212> TYPE: PRT
<213> ORGANISM: Phrixothrix hirtus

<400> SEQUENCE: 4

Met Glu Glu Glu Asn Val Val Asn Gly Asp Arg Pro Arg Asp Leu Val
 1               5                  10                  15

Phe Pro Gly Thr Ala Gly Leu Gln Leu Tyr Gln Ser Leu Tyr Lys Tyr
            20                  25                  30

Ser Tyr Ile Thr Asp Gly Ile Ile Asp Ala His Thr Asn Glu Val Ile
        35                  40                  45

Ser Tyr Ala Gln Ile Phe Glu Thr Ser Cys Arg Leu Ala Val Ser Leu
    50                  55                  60

Glu Lys Tyr Gly Leu Asp His Asn Asn Val Val Ala Ile Cys Ser Glu
65                  70                  75                  80

Asn Asn Ile His Phe Phe Gly Pro Leu Ile Ala Ala Leu Tyr Gln Gly
                85                  90                  95

Ile Pro Met Ala Thr Ser Asn Asp Met Tyr Thr Glu Arg Glu Met Ile
            100                 105                 110

Gly His Leu Asn Ile Ser Lys Pro Cys Leu Met Phe Cys Ser Lys Lys
        115                 120                 125

Ser Leu Pro Phe Ile Leu Lys Val Gln Lys His Leu Asp Phe Leu Lys
    130                 135                 140

Arg Val Ile Val Ile Asp Ser Met Tyr Asp Ile Asn Gly Val Glu Cys
145                 150                 155                 160

Val Phe Ser Phe Asp Ser Arg Asn Thr Asp His Ala Phe Asp Pro Val
                165                 170                 175

Lys Phe Asn Pro Lys Glu Phe Asp Pro Leu Glu Arg Thr Ala Leu Ile
            180                 185                 190

Met Thr Ser Ser Gly Thr Thr Gly Leu Pro Lys Gly Val Val Ile Ser
        195                 200                 205

His Arg Ser Ile Thr Ile Arg Phe Val His Ser Ser Asp Pro Ile Tyr
    210                 215                 220

Gly Thr Arg Ile Ala Pro Asp Thr Ser Ile Leu Ala Ile Ala Pro Phe
225                 230                 235                 240

His His Ala Phe Gly Leu Phe Thr Ala Leu Ala Tyr Phe Pro Val Gly
                245                 250                 255

Leu Lys Ile Val Met Val Lys Lys Phe Glu Gly Glu Phe Phe Leu Lys
            260                 265                 270
```

―continued

```
Thr Ile Gln Asn Tyr Lys Ile Ala Ser Ile Val Val Pro Pro Pro Ile
        275                 280                 285

Met Val Tyr Leu Ala Lys Ser Pro Leu Val Asp Glu Tyr Asn Cys Ser
        290                 295                 300

Ser Leu Thr Glu Ile Ala Ser Gly Gly Ser Pro Leu Gly Arg Asp Ile
305                 310                 315                 320

Ala Asp Lys Val Ala Lys Arg Leu Lys Val His Gly Ile Leu Gln Gly
                325                 330                 335

Tyr Gly Leu Thr Glu Thr Cys Ser Ala Leu Ile Leu Ser Pro Asn Asp
                340                 345                 350

Arg Glu Leu Lys Lys Gly Ala Ile Gly Thr Pro Met Pro Tyr Val Gln
            355                 360                 365

Val Lys Val Ile Asp Ile Asn Thr Gly Lys Ala Leu Gly Pro Arg Glu
        370                 375                 380

Lys Gly Glu Ile Cys Phe Lys Ser Gln Met Leu Met Lys Gly Tyr His
385                 390                 395                 400

Asn Asn Pro Gln Ala Thr Arg Asp Ala Leu Asp Lys Asp Gly Trp Leu
                405                 410                 415

His Thr Gly Asp Leu Gly Tyr Tyr Asp Glu Asp Arg Phe Ile Tyr Val
                420                 425                 430

Val Asp Arg Leu Lys Glu Leu Ile Lys Tyr Lys Gly Tyr Gln Val Ala
                435                 440                 445

Pro Ala Glu Leu Glu Asn Leu Leu Leu Gln His Pro Asn Ile Ser Asp
        450                 455                 460

Ala Gly Val Ile Glu Phe Arg Thr Asn Leu Leu Val Asn Tyr Leu Ser
465                 470                 475                 480

Ala Cys Val Val Leu Glu Pro Gly Lys Thr Met Thr Glu Lys Glu Val
                485                 490                 495

Gln Asp Tyr Ile Ala Glu Leu Val Thr Thr Thr Lys His Leu Arg Gly
                500                 505                 510

Gly Val Val Phe Ile Asp Ser Ile Pro Lys Gly Pro Thr Gly Lys Leu
            515                 520                 525

Met Arg Asn Glu Leu Arg Ala Ile Phe Ala Arg Glu Gln Ala Lys Ser
        530                 535                 540

Lys Leu
545
```

US 6,962,986 B2

NUCLEIC ACID MOLECULES ENCODING RED AND GREEN EMITTING LUCIFERASES

RELATED APPLICATIONS

This application is a continuation of U.S. application Ser. No. 09/516,958, filed Mar. 1, 2000, now abandoned, which is a continuation-in-part of U.S. application Ser. No. 09/388,290, filed Sep. 1, 1999, now abandoned, which claims priority to Italian application 5339, filed Sep. 2, 1998, the contents of which are incorporated herein by reference in their entirety.

BACKGROUND OF THE INVENTION

Bioluminescence in beetles is characterized by a widerange of colors. Fireflies (Lampyridae) emit in the green-yellow region of the spectrum (1, 2), click-beetles (Elateridae) emit in the green-orange (2, 3), but railroad-worms (Phengodidae) span the widest range of the spectrum, that is, from the green to the red region (4, 5). The emission of green-red light was suggested to be an adaptation to optimize the detection of bioluminescence in distinct photic environments and for different biological functions (6). In all cases, such distinct colors arise from structurally homologous luciferases, which catalyze the same ATP-dependent oxidation of D-luciferin (7). Most studies about the structure and function of beetle luciferases have focused on a set of luciferases arising mainly from fireflies (8–14), two click-beetle species (15, 16), and recently a North American species of *Phengodes* (17). Three main factors at the level of the luciferase active site are believed to govern bioluminescence colors (7): (I) the presence of basic residues catalyzing tautomerization between a ketonic (red light emitter) and enolic (yellow-green light emitter) species of excited oxy-luciferin (18–20); (II) the hydrophobicity of the active site (21, 22); and (III) the active site conformation which affects rotation of excited oxyluciferin along the $C_2$–$C_2'$ bond (23). These factors may act together or independently to determine distinct bioluminescence colors in luciferases of different species. The construction of chimeric proteins using click-beetle luciferases (24) and firefly luciferases (25), along with mutagenesis studies (26–28), have revealed important regions and key residues for the bioluminescence color determination. The crystallographic structure of firefly luciferase has been recently resolved in the absence of the substrates (29), which shows a main N-terminal domain and a smaller C-terminal cleft which supposedly come closer to sandwich the substrates during catalysis. Despite all these studies, no structural investigations had been conducted on naturally occurring red light-emitting luciferases.

The beautiful and rare *Phrixothrix* railroad-worms are probably the most spectacular luminescent beetles, because in addition to their yellow-green bioluminescence ($\lambda_{max}$=542–574 nm), displayed by two sets of 11 dorsal-lateral lanterns along the body, they emit red bioluminescence ($\lambda_{max}$=609–638 nm) through cephalic and postcephalic organs (4, 5), a unique property among terrestrial creatures. The function of the lateral lantern bioluminescence is probably associated with defensive and sexual attraction purposes, whereas in the case of the red lantern bioluminescence was associated with self-illumination (5); however experimental evidence is still lacking. Due to their scarcity, only preliminary biochemical studies have been conducted about these creature luciferases (4, 20). Railroad-worm and click-beetle luciferases share a common feature: they do not suffer batchromic shift upon decreasing pH as lampyrid luciferases do (20). Due to their peculiar spectral properties, *Phrixothrix* luciferases constitute very important models for understanding the mechanism of color modulation in beetle bioluminescence.

SUMMARY OF THE INVENTION

The invention describes the cloning of the cDNAs arising from the beetles *Phrixothrix vivianii* and *Phrixothrix hirtus*, which code the luciferases that catalyze the production of green and red light, respectively. These cDNAs were characterized by their respective sequences of SEQ ID NOs:1 and 3, along with their deduced amino acid sequences of SEQ ID NOs: 2 and 4, respectively.

Thus, the present invention relates to an isolated nucleic acid molecule comprising a nucleotide sequence selected from the group consisting of SEQ ID NO:1 and SEQ ID NO:3 and the complement of SEQ ID NO:1 and SEQ ID NO:3. The invention further relates to a nucleic acid molecule which hybridizes under high stringency conditions to a nucleotide sequence selected from the group consisting of SEQ ID NO:1 and SEQ ID NO:3 and the complement of SEQ ID NO:1 and SEQ ID NO:3.

The invention also relates to a vector comprising an isolated nucleic acid molecule of the invention operatively linked to a regulatory sequence, as well as to a recombinant host cell comprising the vector. The invention also provides a method for preparing a polypeptide encoded by an isolated nucleic acid molecule, comprising culturing a recombinant host cell (e.g., bacterial, fungal, plant, insect and mammalian cells) of the invention under conditions suitable for expression of said nucleic acid molecule.

The invention further provides an isolated polypeptide encoded by isolated nucleic acid molecules of the invention. In a particular embodiment, the polypeptide comprises the amino acid sequence of SEQ ID NO: 2 or SEQ ID NO: 4. The invention also relates to an isolated polypeptide comprising an amino acid sequence which is greater than about 80 percent identical and more specifically 90 percent identical to the amino acid sequence of SEQ ID NO: 2 or SEQ ID NO: 4.

The invention also relates to an antibody, or an antigen-binding fragment thereof, which selectively binds to the polypeptides of the invention, as well as to a method for assaying the presence of a polypeptide encoded by an isolated nucleic acid molecule of the invention in a sample, comprising contacting said sample with an antibody which specifically binds to the encoded polypeptide.

Figure 1:
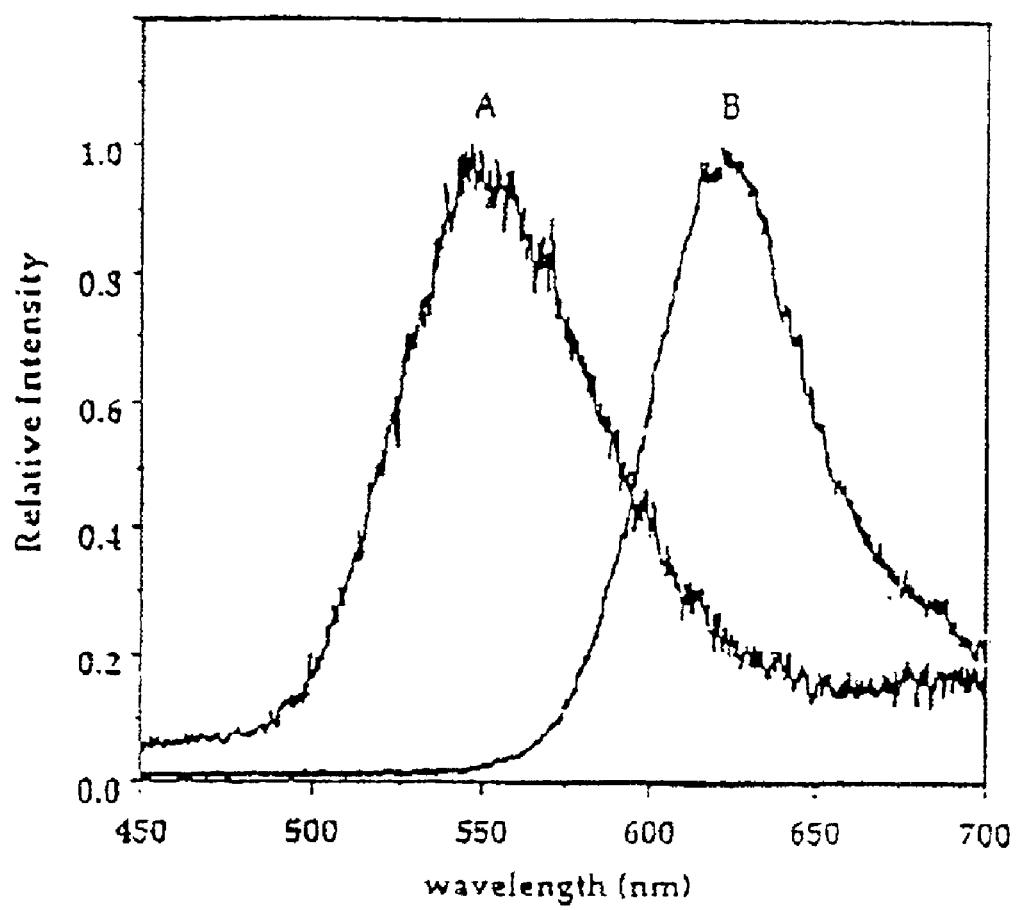
FIG. 1 is an in vitro bioluminescence spectra elicited by *Phrixothrix* railroad-worms recombinant luciferases: (A) $Pv_{GR}$ and (B) $Ph_{RE}$. The BL reactions were conducted on 0.1 M Tris-HCl buffer, pH 8.0. These spectra were corrected for the spectral photosensitivity of the equipment and normalized.

The foregoing and other objects, features and advantages of the invention will be apparent from the following more particular description of preferred embodiments of the invention.

DETAILED DESCRIPTION OF THE INVENTION

*Phrixothrix* railroad-worms emit yellow-green light through 11 pairs of lateral lanterns along the body and red light through two cephalic lanterns. The cDNAs for the lateral lanterns luciferase of *Phrixothrix vivianii*, which emit green light ($\lambda_{max}$=542 nm), and for the head lanterns of *P. hirtus*, which emit the most red-shifted bioluminescence ($\lambda_{max}$=628 nm) among luminescent beetles, were cloned. Positive clones which emitted green (Pv$_{GR}$: $\lambda_{max}$=549 nm) and red (Ph$_{RE}$: $\lambda_{max}$=622 nm) bioluminescence were isolated. The lucifereases coded by Pv$_{GR}$ (545 amino acid residues) and Ph$_{RE}$ (546 amino acid residues) cDNAs share 71% identity. PvGR and PhRE luciferases showed 50–55% and 46–49% identity with firefly luciferases, respectively, and 47–49% with click-beetle luciferases. Ph$_{RE}$ luciferase has some unique residues which replace invariant residues in other beetle luciferases. The additional residue Arg 352 in Ph$_{RE}$, which is deleted in Pv$_{GR}$ polypeptide, seems to be another important structural feature associated with red light production. As in the case of other railroad-worms and click-beetle luciferases studied, *Phrixothrix* luciferases do not undergo the typical red shift suffered by firefly luciferases upon decreasing pH, a property which might be related to the many amino acid residues shared in common between railroad-worm and click-beetle luciferase.

The complete cDNA nucleotidic sequences and the respective amino-acid sequences are shown in the universal genetic code. The region of the cDNA sequences which code for the luciferases (open reading frames) are shown in bold. The ATG start codons as well as the TAA stop codons are underlined.

In addition to the nucleotidic cDNA sequences, and the respective amino-acid sequences of the proteins, the two relevant properties that characterize the biological activity of these proteins (luciferases), are the catalysis of bioluminescence of distinct colors through the oxidation of the same substrate, the firefly D-luciferin [D-2-(6'hydroxy-2'benzothiaxolyl)$\Delta^2$-thiazoline-4-carboxylic acid], as follows:

luciferase coded by *Phrixothrix vivianii* cDNA which produce green light (with maximum of electromagnetic spectrum centered at $\lambda_{max}$=549 nm)

luciferase coded by *Phrixothrix hirtus* cDNA which produce red light (with maximum of electromagnetic spectrum centered at $\lambda_{max}$=622 nm; other cloned luciferases emit in the range between $\lambda_{max}$=546–593 nm of the spectrum).

Comparison of *Phrixothrix* Luciferases.

Although a *Phengodes* luciferase had already been cloned, the sequences of *Phrixothrix* are the first ones of Phengodidae to be reported. The identity between *Phrixothrix* luciferases (71%) is lower than that expected for proteins of different species of the same genus, usually above 80% in the case of click-beetle (16) and of firefly (11, 13) luciferases. Some dissimilarity must result from the divergence of these luciferases toward the emission of distinct bioluminescence colors for the distinct biological functions played by the lateral and head lanterns. Indeed, the luciferase of *R. ohbai* railroad-worm, which arises from lateral lanterns with function and bioluminescence colors similar to those of *P. vivianii* railroad-worm lateral lanterns (37), showed higher identity with Pv$_{GR}$ luciferase (66%) than with Ph$_{RE}$ luciferase (56%) that emits a color very different from that of a distinct lantern.

Comparison of *Phrixothrix* luciferases with a set of 12 other beetle luciferases showed 118 invariant residues, most of them located in the C-terminal region. Beside these invariant residues, *Phrixothrix* luciferases showed 21 additional residues in common with click-beetle luciferases and 31 residues with firefly luciferases. Most of the residues in common with click-beetle luciferases are located in the region between residues 242 and 333, whereas those in common with firefly luciferases are preferentially located in the region between residues 310 and 350. The peroxisomal targeting tripeptide SKL was found in all railroad-worm and click-beetle luciferases and in most firefly luciferases.

Residues Typical of Ph$_{RE}$ Luciferase.

The region from residue 300 to about 480 appears to be more homologous with PvGR and *R. ohbai* green light-emitting luciferases than with Ph$_{RE}$ luciferase. In Ph$_{RE}$ luciferase, the occurrence of many unique substitutions in this otherwise conserved region suggests that this region plays some role in the bioluminescence color determination. The substitution of Ala314 by Ser in Ph$_{RE}$ luciferase is located in a fragment which supposedly interacts with luciferin according to a recently proposed model (42). Whereas substitution of Ala 314 by Ser is associated with considerable chemical changes, the substitution of Ile410 by Leu (Ph$_{RE}$ numbering), except for sterical hindrance effects, does not seem to have considerable influence since these residues have very similar chemical properties. Other substitutions lie in the region 430–480, mainly in the fragment 469–479 which displays a quite hydrophilic character in relation to other luciferases. In click-beetle isoenzymes, which emit such different colors as green and orange, this fragment is invariable and thus does not account for color determination. If such substitutions influence bioluminescence spectra through a cumulative effect, it is more likely that they do so through influencing the conformation of active site, rather than through a solvent effect, since no trend indicative of a relationship between hydropathy profiles and bioluminescence colors was found. Furthermore, the solvent effect created by many substitutions on the active site, although influencing short-range spectral shifts (<40 nm), is not enough only by itself to explain green-red shift, since fluorescence studies on oxyluciferin, dehydroluciferin, and analogues, in solvents with distinct dielectric constants, failed to get such a large spectral shift as that observed in *Phrixothrix* luciferases (>70 nm) (45, 46).

The presence of Arg352 in Ph$_{RE}$ luciferase, which corresponds to the deleted residue in the shorter Pv$_{GR}$ luciferase, is another important distinctive structural feature between these proteins. In PhRE this region (residues 350–362) is associated with a large increase of hydrophobicity in relation to Pv$_{GR}$ luciferase. Such a feature could be potentially involved with considerable conformational changes among these luciferases. Such changes could affect the bioluminescence colors through proper positioning a basic residue in the neighbors of C-5 of excited oxyluciferin in the case of yellow-green-emitting luciferases (20), or by influencing the active site geometry according to hypothesis III (23).

Comparison of *Phrixothrix* Luciferases with Firefly Luciferase Red Mutants.

Other residues whose mutation in firefly luciferases results in red light (26–28) were compared with Ph$_{RE}$ and Pv$_{GR}$ luciferases. Ser286, whose substitution by Asn in the firefly luciferase results in a red shift (26), was found to be conserved in Ph$_{RE}$ luciferase, but replaced by Thr in Pv$_{GR}$ and *R. ohbai* luciferases. Because Ser and Thr have very similar properties, these distinct residues do not seem to be related with determination of bioluminescence color in *Phrixothrix* luciferases. Gly 326, which is replaced by Ser in the firefly red mutant CM-2 (26), was found to be conserved among firefly luciferases, but it was replaced by Ala in all railroad-worm and click-beetle luciferases studied. Thus these substitutions cannot account for red bioluminescence in $Ph_{RE}$ such as in the case of firefly luciferase mutants, probably because changes at these positions affect differently the tridimensional structure of these luciferases. Indeed, the substitutions in the red mutants always involved replacements of charged or polar groups, which can potentially interact with other residues in the tertiary structure of the firefly luciferase through electrostatic interactions or by hydrogen bonding, to keep a conformation necessary for yellow-green light emission. Also, no particular similarities were found between $Ph_{RE}$ luciferase and P. plagiophthalamus orange light-emitting isoenzyme, which emits closer bioluminescence color ($\lambda_{max}$=593 nm). $Ph_{RE}$ and $Pv_{GR}$ luciferases showed independently the same degree of homology with both P. plagiophthalamus green and orange bioluminescence-emitting isoenzymes.

Nucleic Acids of the Invention.

In view of the foregoing, the invention pertains to isolated nucleic acid molecules comprising nucleotide sequences encoding railroad worm luciferases, and the complement of these isolated nucleic acid molecules. The nucleic acid molecules can be double-stranded or single-stranded; single stranded nucleic acid molecules can be either the coding (sense) strand or the non-coding (antisense) strand. The nucleic acid molecules can additionally contain a marker sequence, for example, a nucleotide sequence which encodes a polypeptide, to assist in isolation or purification of the polypeptide. Such sequences include, but are not limited to, those which encode a glutathione-S-transferase (GST) fusion protein and those which encode a hemaglutinin A (HA) peptide marker from influenza. In a preferred embodiment, the nucleic acid molecule has the sequence shown in SEQ ID NO1 or SEQ. ID No:3.

As used herein, an "isolated" or "substantially pure" gene or nucleic acid molecule is intended to mean a gene which is not flanked by nucleotide sequences which normally (in nature) flank the gene (as in other genomic sequences). Thus, an isolated gene can include a gene which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the luciferase gene in tissue (e.g., human tissue), such as by Northern blot analysis.

The present invention also encompasses variations of the nucleic acid sequences of the invention. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the railroadworm luciferases described herein.

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also relates to fragments of the isolated nucleic acid molecules described herein. The term "fragment" is intended to encompass a portion of a nucleic acid sequence described herein which is from at least about 25 contiguous nucleotides to at least about 50 contiguous nucleotides or longer in length. One or more introns can also be present. Such fragments are useful as probes, e.g., for diagnostic methods, as described below and also as primers or probes. Particularly preferred primers and probes selectively hybridize to a nucleic acid molecule containing the luciferase genes described herein.

The invention also pertains to nucleic acid molecules which hybridize under high stringency hybridization conditions, such as for selective hybridization, to a nucleotide sequence described herein (e.g., nucleic acid molecules which specifically hybridize to a nucleic acid containing the luciferase genes described herein). Hybridization probes are oligonucleotides which bind in a base-specific manner to a complementary strand of nucleic acid. Suitable probes include polypeptide nucleic acids, as described in (Nielsen et al., Science 254:1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in Current Protocols in Molecular Biology (Ausubel, F. M. et al., "Current Protocols in Molecular Biology", John Wiley & Sons, (1998)) the teachings of which are hereby incorporated by reference. The exact conditions which determine the stringency of hybridization depend not only on ionic strength (e.g., 0.2× SSC, 0.1× SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, Methods in Enzymology, 200:546–556

(1991). Also, in, Ausubel, et al., "Current Protocols in Molecular Biology", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1%SDS for 15 min at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

Hybridizable nucleic acid molecules are useful as probes and primers, e.g., for diagnostic applications, as described below. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 70%, and more preferably at least about 80% identity, and even more preferably at least about 90% identity, with nucleotide sequences described herein. Particularly preferred in this instance are nucleotide sequences encoding railroad-worm luciferases.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al. (Proc. Natl. Acad. Sci. USA, 90:5873–5877 (1993)). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al. (Nucleic Acids Res, 25:3389–3402 (1997)). When utilizing BLAST and Gapped BLAST programs, the default parameters of the respective programs (e.g., NBLAST) can be used. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

In a related aspect, the nucleic acid fragments of the invention are used as probes or primers in assays such as those described herein. "Probes" are oligonucleotides that hybridize in a base-specific manner to a complementary strand of nucleic acid molecules. Such probes include polypeptide nucleic acids, as described in Nielsen et al., Science, 254, 1497–1500 (1991). Typically, a probe comprises a region of nucleotide sequence that hybridizes under highly stringent conditions to at least about 15, typically about 20–25, and more typically about 40, 50 or 75, consecutive nucleotides of a nucleic acid molecule comprising a nucleotide sequence selected from SEQ ID NOs: 1 or 3, the complement of SEQ ID NOs: 1 or 3. More typically, the probe further comprises a label, e.g., radioisotope, fluorescent compound, enzyme, or enzyme co-factor.

The invention also provides expression vectors containing a nucleic acid comprising the luciferase genes, operatively linked to at least one regulatory sequence. Many such vectors are commercially available, and other suitable vectors can be readily prepared by the skilled artisan. "Operatively linked" is intended to mean that the nucleic acid sequence is linked to a regulatory sequence in a manner which allows expression of the nucleic acid sequence. Regulatory sequences are art-recognized and are selected to produce the luciferases described herein. Accordingly, the term "regulatory sequence" includes promoters, enhancers, and other expression control elements such as those described in Goeddel, Gene Expression Technology: Methods in Enzymology 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the receptor desired to be expressed. For instance, the gene of the present invention can be expressed by ligating the gene into a vector suitable for expression in either prokaryotic cells, eukaryotic cells or both (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Vectors can also include, for example, an autonomously replicating sequence (ARS), expression control sequences, ribosome-binding sites, RNA splice sites, polyadenylation sites, transcriptional terminator sequences, secretion signals and mRNA stabilizing sequences.

Prokaryotic and eukaryotic host cells transformed by the described vectors are also provided by this invention. For instance, cells which can be transformed with the vectors of the present invention include, but are not limited to, bacterial cells such as *E. coli* (e.g., *E. coli* K12 strains), *Streptomyces, Pseudomonas, Serratia marcescens* and *Salmonella typhimurium*, insect cells (baculovirus), including *Drosophila*, fungal cells, such as yeast cells, plant cells and mammalian cells, such as thymocytes, Chinese hamster ovary cells (CHO), and COS cells. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host.

The nucleic acid molecules of the present invention can be produced, for example, by replication in a suitable host cell, as described above. Alternatively, the nucleic acid molecules can also be produced by chemical synthesis.

The nucleotide sequences of the nucleic acid molecules described herein (e.g., a nucleic acid molecule comprising SEQ ID NO:1 or SEQ ID NO:3) can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), and self-sustained sequence replication (Guatelli et al., *Proc. Nat. Acad. Sci. USA,* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabeled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual,* (Acad. Press, 1988)). Using these or similar methods, the protein(s) and the DNA encoding the protein can be isolated, sequenced and further characterized.

Antisense nucleic acid molecules of the invention can be designed using the nucleotide sequences of the present invention and the complements thereof, and constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

The host cells of the invention can also be used to produce nonhuman transgenic animals. For example, in one embodiment, a host cell of the invention is a fertilized oocyte or an embryonic stem cell into which a nucleic acid molecule of the invention has been introduced. Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens and amphibians. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo* (Cold Spring Harbor Laboratory Press, Cold Spring Harbor, N.Y., 1986). Methods for constructing homologous recombination vectors and homologous recombinant animals are described further in Bradley (1991) *Current Opinion in Bio/Technology,* 2:823–829 and in PCT Publication Nos. WO 90/11354, WO 91/01140, WO 92/0968, and WO 93/04169. Clones of the non-human transgenic animals described herein can also be produced according to the methods described in Wilmut et al (1997)

*Nature*, 385:810–813 and PCT Publication Nos. WO 97/07668 and WO 97/07669.

Peptides and Proteins of the Invention

The present invention also provides isolated polypeptides and variants and fragments thereof that are encoded by the nucleic acid molecules of the invention. For example, as described above, the nucleotide sequences can be used to design primers to clone and express cDNAs encoding the polypeptides of the invention.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the protein preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid molecule comprising a nucleotide sequence selected from the group consisting of SEQ ID NO: 1, SEQ ID NO: 3 and complements and portions thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide encoded by a nucleic acid molecule comprising a nucleotide sequence selected from the group consisting of SEQ ID NO: 1, SEQ ID NO: 3 and complements and portions thereof. Variants also include proteins substantially homologous or identical to these polypeptides but derived from another organism, i.e., an ortholog. Variants also include proteins that are substantially homologous or identical to these polypeptides that are produced by chemical synthesis. Variants also include proteins that are substantially homologous or identical to these polypeptides that are produced by recombinant methods.

As used herein, two proteins (or a region of the proteins) are substantially homologous or identical when the amino acid sequences are at least about 45–55%, typically at least about 70–75%, more typically at least about 80–85%, and most typically greater than about 93% or more homologous or identical. A substantially homologous amino acid sequence, according to the present invention, will be encoded by a nucleic acid molecule hybridizing to SEQ ID NO: 1, SEQ ID NO: 3 or portion thereof, under stringent conditions as more particularly described above.

To determine the percent homology or identity of two amino acid sequences, or of two nucleic acid sequences, the sequences are aligned for optimal comparison purposes (e.g., gaps can be introduced in the sequence of one protein or nucleic acid molecule for optimal alignment with the other protein or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., *Science* 247:1306–1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science*, 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., *J. Mol. Biol.,* 224:899–904 (1992); de Vos et al. *Science,* 255:306–312 (1992)).

The invention also includes polypeptide fragments of the polypeptides of the invention. Fragments can be derived from a polypeptide encoded by a nucleic acid molecule comprising SEQ ID NO: 1, SEQ ID NO: 3 or a portion thereof and the complements thereof. However, the invention also encompasses fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide-specific antibodies.

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a polypeptide of the invention operatively linked to a heterologous protein having an amino acid sequence not substantially homologous to the polypeptide. "Operatively linked" indicates that the polypeptide protein and the heterologous protein are fused in-frame. The heterologous protein can be fused to the N-terminus or C-terminus of the polypeptide. In one embodiment the fusion protein does not affect function of the polypeptide per se. For example, the fusion protein can be a GST-fusion protein in which the polypeptide sequences are fused to the C-terminus of the GST sequences. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant polypeptide. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., *Journal of Molecular Recognition,* 8:52–58 (1995) and Johanson et al., *The Journal of Biological Chemistry,* 270,16:9459–9471 (1995). Thus, this invention also encompasses soluble fusion proteins containing a polypeptide of the invention and various portions of the constant regions of heavy or light chains of immunoglobulins of various subclass (IgG, IgM, IgA, IgE).

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., *Current Protocols in Molecular Biology,* 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide protein.

The isolated polypeptide can be purified from cells that naturally express it, purified from cells that have been altered to express it (recombinant), or synthesized using known protein synthesis methods. In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

In general, polypeptides or proteins of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for cells or tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

In another aspect, the invention provides antibodies to the polypeptides and polypeptide fragments of the invention, e.g., having an amino acid sequence encoded by a nucleic acid molecule comprising all or a portion of SEQ ID NO: 1 or SEQ ID NO: 3. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature,* 256:495–497, the human B cell hybridoma technique (Kozbor et al. (1983) *Immunol. Today,* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology,* supra; Galfre et al. (1977) *Nature,* 266:55052; R. H. Kenneth, in *Monoclonal Antibodies: A New Dimension In Biological Analyses,* Plenum Publishing Corp., New York, N.Y. (1980); and Lerner (1981) *Yale J. Biol. Med.,* 54:387–402. Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System,* Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology,* 9:1370–1372; Hay et al. (1992) *Hum. Antibod. Hybridomas,* 3:81–85; Huse et al. (1989) *Science,* 246:1275–1281; Griffiths et al. (1993) *EMBO J.,* 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

Applicability.

Nucleic acid molecules of this invention can be used as sensitive and versatile tools to report molecular events genetically regulated inside living cells and their extracts in biological assays. (See Gould and Subramani, 1988). The luciferase genes can be ligated to DNA vectors (such as plasmids and virus) downstream regulator elements called promoters, and inserted inside the cells. Under the proper conditions, the promoter will drive the transcription of the luciferase gene and the expression of active luciferases in a manner that is dependent of the degree of activation of the promoter. The expression of the luciferase is directly proportional to the amount of light produced in presence of exogenously supplied D-luciferin and ATP (present in the intracellular medium) and can be quantified using commercially available photometers, such as luminometers. Based on this principle, luciferase genes can be used to monitor the transcriptional activity of promoters, to diagnostic and quantify the spreading of viral infections in animal and vegetal tissues or to diagnostic the presence of virus in biological samples. In this case, the luciferase gene is ligated to a DNA vector downstream a viral promoter, which drives the transcription and expression of luciferase. This system is then introduced inside the cell or the biological sample to be tested. If the biological sample is infected by the virus from which the promoter was isolated, the molecular signals resulting from such virus will activate the promoter that will start to transcribe the luciferase gene and to express luciferase, whose light will confirm the infection. In addition, the amount of light produced will be proportional to the degree of promoter activation which can be used to quantify the titer of the infection (this methodology was already successfully used to detect the presence of virus such as HIV). In brief, luciferase genes can be used as reporter genes for the following purposes: (1) promoter transcriptional activity determination (e.g., single and dual promoters); (2) viral diagnostics and quantification; (3) in vivo expression and visualization in (through) mammalian tissues such as blood, bone tissue and muscular tissue; (3) cytotoxcicity tests; (4) cell viability determination; (5) ATP quantification in biological samples; (6) biosensor for environmental and chemical stress agents, among others. See Gould and Subramani, 1988; Schwartz et al., 1990; Contag et al., 1995; Comhaire et al., 1989; Stanley, 1989; Lundin et al., 1989; Tauriainen et al., 1999.

In the past, only the gene for the luciferase of the North-American firefly *Photinus pyralis*, which produces yellow-green light, has been widely applied as reporter gene. One disadvantage of this reporter gene is that the yellow-green light is considerably absorbed in certain biological samples with high optical density in the blue-yellow region of the spectrum such as the blood and other highly pigmented biological samples. Other genes that code for beetle luciferases that emit in the green-orange region of the spectrum were also cloned (Wood, 1995), but they were not widely used and they suffer similar limitations in pigmented biological samples.

The gene of the red emitting luciferase arising from *Phrixothrix* described herein (Viviani et al, 1999; incorporated herein in its entirety) offer a notable wider potential for application, mainly for purposes of detecting light in biological samples with high optical density in the blue-yellow region of the spectrum such as blood, bone tissue and muscular tissue among others. In addition, the simultaneous use of the genes for the green and red emitting luciferases, with the aim to monitor two different promoters (regulator elements) at the same time, offer the possibility to use 2 reporter genes whose signals can be clearly distinguished by the color of the light, with a minimum of bioluminescence spectrum overlap (<10%) avoiding interferences. Furthermore, both luciferases, arising from the same bioluminescent system, work under the same biochemical conditions (in presence of ATP, magnesium ions which are natural intracellular components) and D-Luciferin which should be supplied exogenously. Since the beetle luciferases genes presently used code for luciferases which produce light in the green-orange range of the spectrum, their simultaneous application is limited by the considerable degree of emission spectra overlapping (>25%), imposing severe difficulties to discriminate one signal from another. One solution to this problem was previously patented by Promega Co. (USA) (Sherf et al., 1996), which used the genes for firefly luciferase which emit yellow-green light and a celenterate (jellyfish) luciferase which emit blue light. However, since these luciferases arise from different bioluminescent systems, they work in distinct biochemical conditions, which is not always a convinient condition.

Thus, the research for efficiency is satisfied by the use of the luciferases coded by the sequences object of this patent application, since they are able to produce the same green and red bioluminescence of *Phrixothrix*, constituting a system which works in the same biochemical conditions and whose bioluminescence spectra have not overlapping.

These genes can also be used for the industrial scale production of luciferases for analytical applications. Light emitted in bioluminescent assays using luciferases is actually detectable by a range of commercially avaliable photometric instruments such as luminometers, photon counters, fluorometers, CCD-camera systems.

The invention will be further illustrated by the following exemplification which is not intended to be limiting in any way.

EXEMPLIFICATIONS

In Vivo Expression of Luciferase by *E. Coli*
Materials and Methods.
Reagents.

Isopropyl-β-D-thiogalactopyranoside (IPTG[1]), 5-bromo-4-chloro-3-indoyl-α-galactopyranoside (X-Gal), dithiothreitol (DTT), D-luciferin (sodium salt), ampicillin, tetracyclin, and kanamycin were from Wako Pure Chemicals (Osaka, Japan); coenzyme-A (CoA) and adenosine triphosphate (ATP) from Oriental Yeast Co (Osaka, Japan); Isogen reagent, restriction enzymes, and Taq polymerase from Nippon Gene (Toyama, Japan); Oligo Tex dT30 and DNA ligation kit from Takara Shuzo (Kyoto, Japan); cDNA synthesis kits from Amersham Pharmacia Biotech (Tokyo, Japan); Gigapack III Gold packaging kit from Stratagene (La Jolla, Calif.); and ABI PRISM Dye terminator Cycle Sequencing kit from Perkin-Elmer (Foster City, Calif.).
Bacterial Strains and Media.

*Echerichia coli* XL1-Blue MRF' and SOLR strains were purchased from Stratagene (La Jolla, Calif.). *E. coli* cells were usually grown in Luria Bertani (LB) medium (1% bacto-triptone, 0.5% yeast extract, 0.5% NaCl). Cell densities were measured by absorbance at 600 nm.
Insects.

Railroad-worms were collected at night as described (5). Larvae of *P. vivianii* were collected in pastures at Fazenda S ão Francisco near Parque Nacional das Emas (prefecture of Mineiros, Goías State). Larvae of *P. hirtus* were collected into cerradão formation at Fazenda Sta Cruz (Costa Rica prefecture, Mato Grosso do Sul State) (31) near the former place. Living specimens were cleaned with distilled water, frozen in liquid nitrogen, and stored at −80° C.
Construction and Screening of cDNA Libraries.

cDNA libraries were constructed using methodology similar to *Pyrearinus termitilluminans* luciferase cloning (16). For *P. vivianii* larvae, total RNA was extracted from the whole bodies (without head) of 8 specimens, yielding 360 μg, using Isogen reagent according established procedures (32). Them RNAs were isolated using Oligo-dT latex in accordance with Kuribayashi et al. (33). cDNAs were synthesized from 4 μg of isolated mRNAs using Time Saver cDNA synthesis kit. The first strand reaction was carried out in the presence of oligo-dT$_{12-18}$ primer. After the synthesis of the second cDNA strand, EcoRI/NotI adaptors were ligated to the blunt ended cDNA. The cDNA (about 50 ng for *P. vivianii* bodies) was ligated to 1 μg of EcoRI pre-digested/dephosphorilated λZAP II (Stratagene, La Jolla, Calif.) vector in a volume of 5 μL of ligation reaction mixture (1 mM ATP, 7 mM MgC$_2$, 1 mM DTT in 50 mM Tris-HCl, pH 8.0, and 1 Weiss unit of T4 ligase) overnight at 16° C. The ligation mixtures were then packaged using Gigapack III Gold packaging extracts. The original library of *P. vivianii* bodies (7.5×10$^5$ pfu) was then in vivo excised into *E. coli* XL1-Blue cells in the presence of helper phage to obtain pBluescript (pB1) libraries. The excised phagemids were used to transform *E. coli* SOLR cells. The plasmid library was screened by photodetection (34) using a cooled-CCD camera system (ATTO; Tokyo, Japan), after spraying 1 mM D-luciferin (0.1 M citrate buffer pH 5.0) onto IPTG induced colonies at 20° C. during 12 h. For *P. hirtus* head lantern library construction, total RNA was extracted from 17 heads and 4 μg of mRNA was used to synthesize cDNA. All other procedures were essentially similar to those described above, except the original library (2.2×10⁴ pfu) was further amplified (1×10⁹ pfu) before excision of the pB1 library.

Sequence Analysis.

The cDNA for green light-emitting luciferase ($Pv_{GR}$), the 0.75 kb long EcoRV/BamHI and BamHI/BamHI fragments were subcloned into pB1 and pUC vectors, respectively (35). The cDNA for red light-emitting luciferase ($Ph_{RE}$) was digested with EcoRI, and the 3 resulting fragments (0.8; 0.6; 0.3 kbp) were subcloned into EcoRI digested/ dephosphorilated pUC 18 vector. All of these constructions and the original luciferase cDNA-containing plasmids were sequenced by the dydeoxy chain termination method (36) using dye-labeled terminator kit specifically developed for the ABI PRISM 377 automatic sequencer (Perkin-Elmer; Foster City-Calif.). For extension of pUC vector, M13 (−21) and reverse primers were used, whereas for pB1 vector T7 and reverse primers were used. Three additional primers, $VA_1$ (5'-ATGTACTTCAATCTCTTTGCTAC-3') (SEQ ID NO:5), $VA_3$ (5'-AAGTCTAACTATAAGATAAGTTCTTA-3') (SEQ ID NO:7), and $VA_4$ (5'-CAAGTTTCAGTTAATCCATAT-3') (SEQ ID NO:6) were designed from the known partial sequences in order to sequence the internal regions of $Ph_{RE}$ and $Pv_{GR}$. Sequence comparisons, multi-alignments, and determination of the protein hydropathy profiles, molecular weights and isoeletric points were made using version 7.3 of Genetyx-mac software (Software Development Co., Ltd., Tokyo, Japan).

Expression and Preparation of Luciferase Extracts.

Liquid cultures of SOLR cells carrying luciferase insert containing pB1 were grown on LB/amp (50 μg/mL) medium at 37° C. with shaking overnight. The preculture (1/100 vol) was then inoculated in LB/amp (50 μg/mL) in the presence of 1 mM IPTG and incubated at 23° C. during 24 h (OD600=1.8). The cells were harvested by centrifugation at 3000 rpm during 10 min at 4° C., and the pellet was resuspended in cold extraction buffer (0.1 M sodium phosphate buffer, pH 7.5, containing 2 mM EDTA, 1 mM DTT, and 1% Triton X-100). Lysozyme was added to the final concentration of 1 mg/mL and the suspension incubated 15 min at 0° C. and frozen at −80° C. during 15 min. The lysate was centrifuged at 12000 g at 4° C. during 15 min. The supernatant was then fractionated with ammonium sulfate. The fraction precipitated between 55% and 70% saturation was dissolved in cold extraction buffer and stored at −20° C. in the presence of glycerol 15%, to maintain the activity.

Luciferase Assays.

The activity levels were measured using a Luminescencer AB-2000 luminometer (Atto; Tokyo, Japan) by integration of total light emitted. The assay consisted of the addition of 50 μL of standard solution (2 mM ATP, 0.5 mM D-luciferin, 4 mM MgSO4 in 0.1 M Tris-HCl buffer, pH 8.0) to 10 μL of luciferase-containing extracts at 25° C. In vivo light intensities were measured after adding 50 μL of 0.5 mM D-luciferin in 0.1 M sodium citrate buffer pH 5.0 to 10 μL of bacterial suspension into a microtiter plate.

Kinetic Measurements.

Measurements of light intensities for KM determinations were made using the luminometer described above. For luciferin KM estimation, 50 μL of 4 mM ATP solution (0.1 M Tris-HCl, pH 8.0, and 8 MM MgSO₄) was injected to 50 μL of crude extract diluted 10 times in 0.1 M Tris-HCl buffer, pH 8.0, containing luciferin (0.03–2 mM). For ATP KM estimation, 50 μL of 0.5 mM luciferin solution (0.1 M Tris-HCl buffer, pH 8.0, 8 mM MgSO4) was injected to 50 μL of 10 times diluted extract containing ATP (0.1–4 mM). The assays were carried out at 25° C. Each point of the Michaelis-Menten curve was assayed in quadruplicate. The KM values were estimated by Lineweaver-Burk plots of the reciprocal of light intensities versus substrate concentration.

Bioluminescence Spectra.

Emission spectra were determined using a Hitachi F4500 spectrofluorometer, supplied with a Hamamatsu Photonics R 928 F photomultiplier, with the excitation lamp shut down. The spectra were automatically corrected for the photosensitivity of the equipment. For bacterial in vivo spectra determinations, 500 μL of bacterial suspension and 500 μL of 0.5 mM D-luciferin in 0.1 M sodium citrate buffer, pH 5.0, and 10 mM MgSO4 were mixed into a cuvette in front of the emission window (16). In vitro spectra were recorded 3 min after mixing 10–100 μL of luciferase-containing extract to 900 μL of standard reaction mixture (0.5 mM D-luciferin, 2 mM ATP, 4 mM MgSO4, 0.5 mM CoA, and 1% Triton X-100 in 0.1 M Tris-HCl uffer, pH 8.0), to a final volume of 1 mL, into a luorometer cuvette (16) in front of the emission window. The pH effect on in vitro spectra was measured in 0.1 M sodium phosphate buffer (pH 6–8) instead of Tris-HCl buffer as described (16). The spectra measured at pH 8.0 in both buffers were essentially identical in shape.

Results

Isolation of Positive Clones and Expression of Active Luciferases.

The *P. vivianii* body cDNA library yielded 7.5×10⁵ recombinant plaques. After screening about 10 000 colonies, we isolated 1 positive clone for light emission ($Pv_{GR}$). The cDNA library for *P. hirtus* head lanterns yielded 2.2×10⁴ recombinant plaques and was amplified (1×10⁹ pfu) before excision. Four positive clones were found after screening 3000 colonies of the excised amplified library. The most intense light-emitting clone ($Ph_{RE}$) was isolated for further analysis. Upon D-luciferin spraying, the IPTG-induced SOLR colonies containing pB1-$Pv_{GR}$ and pB1-$Ph_{RE}$ displayed weak green and red bioluminescence, respectively, visible after dark-room eye adaptation. The luminescence maximum intensity of pB1-$Ph_{RE}$-containing colonies was reached before and decayed sooner than that of pB1-$Pv_{GR}$-containing colonies. Luminometer measurement of the total light output of both in in vivo and in vitro bioluminescence assays of IPTG-induced colonies gave nearly the same values for $Pv_{GR}$ and $Ph_{RE}$ luciferases, after correction for the spectral photosensitivity of the equipment.

cDNAs Structures and Sequences.

The $PV_{GR}$ cDNA (NCBI access number: AF139644) is a 1765 bp long fragment. The start codon was found 25 bp downstream from the cDNA 5'terminus, which follows the PstI restriction site of pBluescript polylinker. An open reading frame of 1635 bp, which codes for a 545 amino acid long polypeptide was found. After the stop codon, a 105 bp long 3' untranslated region followed by a terminal 26 bp poly-A tail was found.

The $Ph_{RE}$ cDNA (NCBI access number: AF139645) is a 1760 bp long fragment. The cDNA has a 41 bp untranslated region upstream from the first ATG. The sequence of the last 10 bp before the starting codon was essentially identical to that of $Pv_{GR}$. An open reading frame of 1638 bp, coding for a potential 546 residue long polypeptide was found. After the stop codon, a 61 bp long downstream untranslated region with a terminal 7 bp long poly-A tail was found.

Protein Sequences.

The overall identity between $Pv_{GR}$ and $Ph_{RE}$ luciferases was 71%. $Pv_{GR}$ and $Ph_{RE}$ luciferases showed 66.6% and 56% identity, respectively, with the Japanese railroad-worm *Ragophthalmus ohbai* luciferase, recently cloned in our laboratory (37). As expected, these values are very close to those observed for *Phengodes* luciferase, with the same set of enzymes (17). $Pv_{GR}$ luciferase showed a slightly higher identity with firefly luciferases (50–55%) than $Ph_{RE}$ did with the same set of enzymes (46–49%). Both luciferases showed 47–49% identity with click-beetle luciferases. The overall identity shared with acyl CoA ligases is 25%. Like most beetle luciferases, both luciferases showed the peroxissomal targeting tripeptide SKL before the stop codons (7).

Protein Properties.

The calculated molecular weights of $Pv_{GR}$ and $Ph_{RE}$ luciferases were 59,626 and 60,951 kDa and were close to those estimated by Western Blotting (data not shown). The isoeletric points, calculated from the deduced primary structures, were 6.26 and 7.0 for $Pv_{GR}$ and $Ph_{RE}$ luciferases, respectively. $Pv_{GR}$ luciferase showed a small increase in the proportion of hydrophobic and neutral residue content in relation to $Ph_{RE}$ luciferase. The hydropathy profiles of these luciferases were similar; however there were some regions which showed major differences. In particular the region from residues 350–360, which includes the additional Arg residue in $Ph_{RE}$ luciferase, showed a major increase of hydrophobic character in $Ph_{RE}$ luciferase in relation to $Pv_{GR}$ luciferase.

Kinetic Parameters.

The $K_M$ values for ammonium sulfate fractionated extracts were measured. For $Ph_{RE}$ luciferase the $K_M$ for luciferin was 20 μM, whereas for ATP it was 240 μM. However for unknown reasons $Pv_{GR}$ luciferase $K_M$ values were much higher than for $Ph_{RE}$ luciferase (150 μM for luciferin and 350 μM for ATP). The rise time to the peak of intensity and the decay rate of in vitro bioluminescence reaction were faster for $Ph_{RE}$ luciferase than for $Pv_{GR}$ (results not shown). A similar property was observed for the time course of the in vivo bioluminescence after spraying D-luciferin.

Spectral Properties.

The in vivo and in vitro bioluminescence spectra emitted by $Pv_{GR}$ luciferase are centered at 549 nm, thus in the green region, close to that reported for the native enzyme extracted from the larval *P. vivianii* lateral lanterns (λmax=542 nm; FIG. 3) (5), and to the spectra emitted by the recently cloned *Phengodes* ($\lambda_{max}$=546 nm) (17) and *R. ohbai* ($\lambda_{max}$556 nm) (37) luciferases. Both the in vivo and in vitro bioluminescence spectra of $Ph_{RE}$ luciferase showed a peak at 622 nm (FIG. 3), thus 73 nm shifted in relation to $Pv_{GR}$ luciferase. The in vitro spectrum is 6 nm blue-shifted in relation to that emitted by the native enzyme extracted from the laval *P. hirtus* head lanterns ($\lambda_{max}$=628 nm) (5), in part due to distinct equipment used for measurements. This spectrum is much narrower (half bandwidth=55 nm) than that emitted by $Pv_{GR}$ luciferase (half-bandwidth=70.5 nm) and other bettle luciferases. The bioluminescence spectra of both recombinant luciferases did not suffer red shift upon decreasing the pH from 8.0 to 6.0, although they underwent a decrease of intensity.

While this invention has been particularly shown and described with references to preferred embodiments thereof, it will be understood by those skilled in the art that various changes in form and details may be made therein without departing from the scope of the invention encompassed by the appended claims.

References

1. Seliger, H. H., Buck, J. B., Fastie, W. G., and McElroy, W. D., *J. Gen. Physiol.* 48:95–104 (1964).
2. Biggley, W. H., Lloyd, J. E., and Seliger, H. H., *J. Gen. Physiol.* 50:1681–1692 (1967).
3. Colepicolo, N. P., Costa, C., and Bechara, E. J. H., *Insect Biochem.* 16, 803–810 (1986).
4. Viviani, V. R., and Bechara, E. J. H., *Photochem. Photobiol.* 58:615–622 (1993).
5. Viviani, V. R., and Bechara, E. J. H., *Ann. Entomol. Soc. Am.* 90:389–398 (1997).
6. Lall, B. A, Seliger, H. H., Biggley, W. H., and Lloyd, J. E., *Science* 210:560–562 (1980).
7. Wood, K. V., *Photochem. Photobiol.* 62:662–673 (1995).
8. De Wet, J. R., Wood, K. V., Helinsky D. R., and DeLuca, M, Proc. Natl. Acad. Sci. U.S.A. 82:, 7870–7873 (1985).
9. Tatsumi, H., Masuda, T., Kajiyama, N., and Nakano, E., *J. Biolum. Chemilum.* 3:75–78 (1989).
10. Tatsumi, H., Kajiyama, N., and Nakano, E., Biochim. Biophys. Acta 1131:, 161–165 (1992).
11. Devine, J. H., Kutuzova, G. D., Green, V. A., Ugarova, N. N., and Baldwin, T. O., Biochim. Biophys. Acta 1173:121–132 (1993).
12. Ohmiya, Y., Ohba, N., Toh, H., and Tsuji, F. I., *Photochem. Photobiol.* 62:309–313 (1995).
13. Sala-Newby, G. B., Thomson, C. M., and Campbell, A. K. (1996) *Biochem. J.* 313, 761–767.
14. Li, Ye, Buck, L. M., Scaeffer, H. J., and Leach, F. R., *Biochim. Biophys. Acta* 1339:39–52 (1997).
15. Wood, K. V., Lam, Y. A., Seliger, H. H., and McElroy, W. D., *Science* 244: 700–702 (1989).
16. Viviani, V. R., Silva, A. C. R., Barbosa, G. N., Perez, G. L. O., Santelli, R. V., Bechara, E. J. H., and Reinach, F. C. Proceedings of the X th International Symposium on Bioluminescence and Chemiluminescence (Apr. –Aug. 09, 1998) Bologna, Italy (1999).
17. Gruber, M. G., Kutuzova, G. D., and Wood, K. V., In *Bioluminescence and Chemiluminescence: Molecular Reporting with Photons.* Proceedings of the 9 th International Sym-posium (Hastings, J. W., Kricka, L. J., Stanley, P. E., Eds.) pp 244–247, John Wiley and Sons, Chichester, U. K (1996).
18. White, E. H., Rapaport, E., Hopkins, T. A., and Seliger, H. H., *J. Am. Chem. Soc.* 91:1243–1245 (1969).
19. White, E. H., and Branchini, B., *J. Am. Chem. Soc.* 97:2178–2180 (1975).
20. Viviani, V. R., and Bechara, E. J. H., Photochem. Photobiol. 62:490–495 (1995).
21. DeLuca, M. (1969) *Biochemistry* 8, 160–166.
22. Brovko, Lyu, Dementieva, E. I., and Ugarova, N. N., In *Bioluminescence and Chemiluminescence: Molecular Re-porting with Photons.* Proceedings of the 9th International Symposium (Hastings, J. W., Kricka, L. J., Stanley, P. E., Eds.) pp 206–211, John Wiley and Sons, Chichester, U. K (1996).
23. McCapra, F., Gilfoyle, D. J., Young, D. W., Church, N. J., and Spencer, P., In *Bioluminescence and Chemiluminescence: Fundamental and Applied Aspects* (Campbell, A. K., Kricka, L. J. Stanley, P. E., Eds.) pp 387–391, John Wiley and Sons, Chichester, U. K (1994).
24. Wood, K. V., *J. Biol. Chemilum.* 5:107–114 (1990).
25. Ohmiya, Y., Hirano, T., and Ohashi, M., *FEBS Lett.* 384:83–86 (1996).
26. Kajiyama, N., and Nakano, E., *Protein Eng.* 4:691–693 (1991).
27. Mamaev, S. V., Laikhter, A. L., Arslan, T., and Hecht, S. M., *J. Am. Chem. Soc.* 118:7243–7244 (1996).
28. Ueda, H., Yamanouchi, H., Kitayama, A., Inoue, K., Hirano, T., Suzuki, E., Nagamune, T., and Ohmiya, Y., In *Bioluminescence and Chemiluminescence: Molecular*

Reporting with Photons. Proceedings of the 9th International Symposium (Hastings, J. W., Kricka, L. J., Stanley, P. E., Eds.) pp 216–219, John Wiley and Sons, Chichester, U. K. (1996).
29. Conti, E., Franks, N. P., and Brick, P., *Structure* 4:287–298 (1996).
30. Wittmer, W., *Mitt. Entomol. Ges.* BRD 42:130–132 (1993).
31. Costa, C., Vanin, S. A., Casari, S. A., and Viviani, V. R. *Ilheringia* (1999).
32. Chomczynsky, P., and Sacchi, N., *Anal. Biochem.* 162:156–159 (1987).
33. Kuribayashi, K., Hirata, M., Kiraoka, O., Miyamoto, C., and Furushi, Y., *Nucleic Acids Symposium Series,* Vol. 1, p 61, Harvard Medical School, John Wiley and Sons, New York (1988).
34. Wood, K. V., and DeLuca, M., *Anal. Biochem.* 161:501–507 (1987).
35. Ausbel, M. F., et al., *Short Protocols in Molecular Biology.* (Ausbel, F. M., Brent, R., Kingston, R. E., Moore, D. D., Seidman, J. G., Smith, J. A., Struhl, K., Eds.) Harvard Medical School, John Wiley and Soons, New York (1992).
36. Sambrook, J., Fritsch, E. F., and Maniatis, T., *Molecular Cloning, a Laboratory Manual,* 2nd ed. Cold Spring Harbor, New York (1989).
37. Sumiya, M., Viviani, V. R., Ohba, N., and Ohmiya, Y., *J. Biolum. Chemilum.* 13:225 (1998).
38. White, E., Rapaport, E., Seliger, H. H., and Hopkins, T. A., *Bioorg Chem.* 1:92–122 (1971).
39. White, E., and Roswell, D. F., *Photochem. Photobiol.* 53:131–136 (1991).
40. Alter, S. C., and DeLuca, M., *Biochemistry* 25:1599–1605 (1986).
41. Branchini, B. R., Magyar, R. A., Marcantonio, K. M., Newberry, K. J., Stroh, J. G., Hinz, L. K., and Murtiashaw, M. H., J. Biol. Chem. 272:19359–19364 (1997).
42. Branchini, B., Magyar, R. A., Murtiashaw, M. H., Anderson, S. M., and Zimmer, M., *Biochemistry* 37:15311–15319 (1998).
43. Conti, E., Stachelhaus, T., Marahiel, M. A., and Brick, P., *EMBO J.* 16:4174–4183 (1997).
44. Seliger, H. H., and McElroy, W. D., Proc. Natl. Acad. Sci. U.S.A. 52:75–81 (1964).
45. DeLuca, M., *Biochemistry* 13:921–925 (1974).
46. Bowie, L. J., Horak, V., and DeLuca, M., *Biochemistry* 8:1598–1607 (1969).
47. Campbell, A K., *Chemiluminescence: principles and applications in biology and medicine,* Ellis Horwood, Cichester, England (1988).
48. Hopp, T. P., and. Woods, K. R., *Proc. Natl. Acad Sci. U.S.A.* 78:3824–3828 (1981).
Comhaire, F. H., L. Vermeulen, L. Monsieur and A. Hinting, "Determination of adenosine triphosphate in human semen to estimate the fertilizing potential and to quantify sperm antibodies", *J. Biolum. Chemilum.* 4:399–405 (1989).
Contag, C. H., Spilman, S. D., Contag, P. R., Oshiro M., Eames B., Dennery P., Stevenson D. H. and D. A. Benaron, "Visualizing gene expression in living mammals using a bioluminescent reporter", *Photochem. Photobiol.* 66:523–531 (1997).
De Wet, J. R., K. V. Wood, D. R. Helinsky and M. DeLuca, "Cloning of firefly luciferase cDNA and expression of active luciferase in *Echerichia coli.",* Proc. Natl. Acad. Sci. USA 82:7870–7873 (1985).
Gould, S. J. and S. Subramani, "Firefly luciferase as a tool in molecular and cell biology", *Anal. Biochem.* 175:5–13 (1988).
Lundin, A., H. Hallander, A. Kallner, U. K. Lundin and E. Osterberg, "Bacteriuria testing by the ATP method as an integral part in the diagnosis and therapy of urinary tract infection (UTI)", *J. Biolum. Chemilum.* 4:381–389 (1989).
Schwartz O., J. L. Virelizier, L. Montagnier and U. Hazan, "A microtransfection method using the luciferase-encoding reporter gene for the assay of human immuno-deficiency virus LTR promoter activity", *Gene* 88:197–205 1990.
Sherf, B. A., S. L. Navarro, R. R. Hannah and K. V. Wood, "Dual-luciferase™ reporter assay: an advanced co-reporter technology integrating firefly and Renilla luciferase assays. *Promega Notes* 57:2–9 (1996).
Stanley, P. E., "A review of the bioluminescent ATP techniques in rapid microbiology", *J. Biolum. Chemilum.* 4:375–380 (1989).
Tautoriainen, S., M. Virta, W. Chang and M. Karpi, "Measurement of firefly luciferase reporter gene activity from cells and lysates using *Escherichia coli* arsenite and mercury sensors", *Anal. Biochem.* 272:191–198 (1999).
Viviani, V. R., E. J. H. Bechara and Y. Ohmiya, "Cloning, sequence analysis, and expression of active *Phrixothrix* railroad-worm luciferases: Relationship between bioluminescence spectra and primary structures", *Biochemistry* 38:8271–8279 (1999).
Wood, K. V., "The chemical mechanism and evolutionary development of beetle bioluminescence", *Photochem. Photobiol.* 62:662–673 (1995).

What is claimed is:

1. An isolated nucleic acid molecule encoding a green light emitting luciferase selected from the group consisting of:

a) a nucleic acid molecule comprising SEQ ID NO:1; and b) a nucleic acid molecule that hybridizes to SEQ ID NO:1 under high stringency conditions comprising washing in a solution containing 0.1×SSC/0.1% SDS for 15 min at 68° C.; or a nucleic acid molecule that is 100% complementary to (a) or (b)

wherein the encoded green light emitting luciferase emits green bioluminescence having a maximum λ of approximately 549 nm when expressed in *E. coli*.

2. A vector comprising the isolated nucleic acid molecule as defined in claim 1.

3. A recombinant host cell comprising the vector as defined in claim 2.

* * * * *

UNITED STATES PATENT AND TRADEMARK OFFICE
CERTIFICATE OF CORRECTION

PATENT NO. : 6,962,986 B2
APPLICATION NO. : 09/993874
DATED : November 8, 2005
INVENTOR(S) : Vadim R. Vivianni and Yoshihiro Ohmiya It is certified that error appears in the above-identified patent and that said Letters Patent is hereby corrected as shown below:

Title Page (73)
    Column 1 (Assignee), Line 1 – Delete "Osaka" and insert -- 2-8, Dojima Hama 2-chome, Kita-ku, Osaka-shi, Osaka-fu, --, therefor.

Title Page (56)
    Column 2 (Other Publications), Line 2 – After "8279." Insert -- (1999) --

Title Page (56)
    Column 2 (Other Publications), Line 8 – Delete "GeneBank" and insert -- AF139644 GenBank --, therefor.

Title Page (56)
    Column 2 (Other Publications), Line 9 – Delete "GeneBank" and insert -- AF139645 GenBank --, therefor.

Title Page (56)
    Column 2 (Other Publications), Line 11 – Delete "app" and insert -- spp --, therefor.

Title Page (56)
    Column 2 (Other Publications), Line 11 – Delete "(Coleoptera:Phenogodidae)" and insert -- (Coleoptera : Phenogodidae) --, therefor.

Title Page (56) page 2
    Column 1 (Other Publications), Line 3 – Delete "Effects" and insert -- Effect --, therefor.

Title Page (56) page 2
    Column 2 (Other Publications), Line 3 – Delete "Viviani" and insert -- Viviani, --, therefor.

Title Page (57)
    Column 2 (Abstract), Line 2 – Delete "Phrixotrhix" and insert -- Phrixothrix --, therefor.

UNITED STATES PATENT AND TRADEMARK OFFICE
CERTIFICATE OF CORRECTION

PATENT NO.        : 6,962,986 B2
APPLICATION NO. : 09/993874
DATED             : November 8, 2005
INVENTOR(S)       : Vadim R. Vivianni and Yoshihiro Ohmiya It is certified that error appears in the above-identified patent and that said Letters Patent is hereby corrected as shown below:

Column 1 (Specification), Line 10 (approx) – Delete "5339," and insert -- ITI998000000195, --, therefor.

Column 1 (Specification), Line 35 – Delete "oxy-luciferin" and insert -- oxyluciferin --, therefor.

Column 3 (Specification), Line 7 – Delete "lucifereases" and insert -- luciferases --, therefor.

Column 4 (Specification), Line 16 – Delete "Ala314" and insert -- Ala 314 --, therefor.

Column 5 (Specification), Line 33 – Delete "NO1" and insert -- NO: 1 --, therefor.

Column 5 (Specification), Line 33 – Delete "SEQ." and insert -- SEQ --, therefor.

Column 8 (Specification), Line 16 – Delete "Res," and insert -- Res., --, therefor.

Column 10 (Specification), Line 46 – Delete "an" and insert -- a --, therefor.

Column 10 (Specification), Line 57 – Delete "and" and insert -- , --, therefor.

Column 10 (Specification), Line 67 – Delete "et al" and insert -- et al. --, therefor.

Column 15 (Specification), Line 44 – Delete "Lemer" and insert -- Lerner --, therefor.

Column 17 (Specification), Line 31 – Delete "et al," and insert -- et al., --, therefor.

Column 17 (Specification), Line 59 – Delete "convenient" and insert

UNITED STATES PATENT AND TRADEMARK OFFICE
CERTIFICATE OF CORRECTION

PATENT NO. : 6,962,986 B2
APPLICATION NO. : 09/993874
DATED : November 8, 2005
INVENTOR(S) : Vadim R. Vivianni and Yoshihiro Ohmiya It is certified that error appears in the above-identified patent and that said Letters Patent is hereby corrected as shown below:

-- convenient --, therefor.

Column 18 (Specification), Line 2 – Delete "available" and insert -- available --, therefor.

Column 18 (Specification), Line 47 – Delete "Them" and insert -- The --, therefor.

Column 19 (Specification), Line 12 – Delete "(PhRE)" and insert -- (Ph$_{RE}$) --, therefor.

Column 19 (Specification), Line 17 – Delete "dydeoxy" and insert -- dideoxy --, therefor.

Column 19 (Specification), Line 36 – Delete "vol)" and insert -- vol.) --, therefor.

Column 19 (Specification), Line 65 – Delete "8 MM" and insert -- 8 mM --, therefor.

Column 20 (Specification), Line 19 – Delete "o.5 mM" and insert -- 0.5 mM --, therefor.

Column 20 (Specification), Line 20 – Delete "uffer," and insert -- buffer, --, therefor.

Column 20 (Specification), Line 44 – After "both in" delete "in".

Column 21 (Specification), Line 10 – Delete "peroxissomal" and insert -- peroxisomal --, therefor.

Column 21 (Specification), Line 43 – Delete "($\lambda$max" and insert -- ( $\lambda_{max}$ --, therefor.

Column 21 (Specification), Line 45 – Delete "($\lambda_{max}$556" and insert-- ($\lambda_{max}$=556 --,

UNITED STATES PATENT AND TRADEMARK OFFICE
CERTIFICATE OF CORRECTION

PATENT NO. : 6,962,986 B2
APPLICATION NO. : 09/993874
DATED : November 8, 2005
INVENTOR(S) : Vadim R. Vivianni and Yoshihiro Ohmiya It is certified that error appears in the above-identified patent and that said Letters Patent is hereby corrected as shown below:

therefor.

Column 22 (Specification), Line 17 – Delete "1131:," and insert -- 1131, --, therefor.

Column 22 (Specification), Line 37 – Delete "Sym-posium" and insert

-- Symposium --, therefor.

Column 22 (Specification), Line 39 – Delete "U. K" and insert -- U. K. --, therefor.

Column 22 (Specification), Line 52 – Delete "U. K" and insert -- U. K. --, therefor.

Column 22 (Specification), Line 57 – Delete "U. K" and insert -- U. K. --, therefor.

Column 38 (Claim 1) – After "(b)" delete "wherein the encoded green light emitting luciferase emits green bioluminescence having a maximum λ of approximately 549 nm when expressed in E coli."

Signed and Sealed this

Seventeenth Day of April, 2007

JON W. DUDAS
*Director of the United States Patent and Trademark Office*